(12) United States Patent
Perez

(10) Patent No.: US 8,544,684 B2
(45) Date of Patent: Oct. 1, 2013

(54) VISUAL, BI-AUDIBLE, AND BI-TACTILE METERED-DOSE TRANSDERMAL MEDICAMENT APPLICATOR

(76) Inventor: Ramiro M. Perez, Folsom, CA (US)

(*) Notice: Subject to any disclaimer, the term of this patent is extended or adjusted under 35 U.S.C. 154(b) by 106 days.

(21) Appl. No.: 13/275,282

(22) Filed: Oct. 17, 2011

(65) Prior Publication Data

US 2012/0205393 A1    Aug. 16, 2012

Related U.S. Application Data

(60) Provisional application No. 61/443,029, filed on Feb. 15, 2011.

(51) Int. Cl.
*B67D 1/00* (2006.01)

(52) U.S. Cl.
USPC ............ 222/39; 222/48; 222/390; 401/175

(58) Field of Classification Search
USPC .............. 222/39, 48, 390; 401/172–175
See application file for complete search history.

(56) References Cited

U.S. PATENT DOCUMENTS

| | | | |
|---|---|---|---|
| 3,333,740 A | 8/1967 | Waller | |
| 3,616,970 A | 11/1971 | Baumann | |
| 3,873,008 A | 3/1975 | Jahn | |
| 4,074,833 A | 2/1978 | Otto | |
| 4,139,127 A | 2/1979 | Gentile | |
| 4,298,036 A | 11/1981 | Horvath | |
| 4,363,560 A | 12/1982 | Gentile | |
| 4,521,127 A * | 6/1985 | Tomburo et al. | 401/68 |
| 4,544,083 A | 10/1985 | Schroeder | |
| 4,595,124 A * | 6/1986 | Duval et al. | 222/39 |
| 4,641,776 A | 2/1987 | Vlasek | |
| 4,658,993 A | 4/1987 | Vlasich | |
| 4,850,516 A | 7/1989 | Seager | |
| 4,865,231 A | 9/1989 | Wiercinski | |
| 5,000,356 A | 3/1991 | Johnson | |
| 5,007,755 A | 4/1991 | Thompson | |
| 5,016,782 A | 5/1991 | Pfanstiel | |
| 5,025,960 A | 6/1991 | Seager | |
| 5,540,361 A | 7/1996 | Fattori | |
| 5,573,341 A | 11/1996 | Iaia | |
| 5,725,133 A | 3/1998 | Iaia | |
| 5,839,622 A | 11/1998 | Bicknell | |
| 5,851,079 A * | 12/1998 | Horstman et al. | 401/174 |
| 5,947,621 A | 9/1999 | Szekely | |
| 6,039,483 A | 3/2000 | Szekely | |
| 6,450,720 B1 * | 9/2002 | Cai | 401/193 |
| 7,086,564 B1 * | 8/2006 | Corrigan | 222/39 |
| 7,213,994 B2 | 5/2007 | Phipps | |
| 7,303,348 B2 * | 12/2007 | Phipps et al. | 401/175 |
| 7,946,780 B2 * | 5/2011 | Zhang | 401/277 |
| 8,292,532 B2 * | 10/2012 | Nasu et al. | 401/175 |

\* cited by examiner

*Primary Examiner* — Kevin P Shaver
*Assistant Examiner* — Daniel R Shearer
(74) *Attorney, Agent, or Firm* — Inventive Patent Law P.C.; Jim H. Salter

(57) ABSTRACT

A bi-audible, bi-tactile, and visual transdermal delivery apparatus for delivering specific desired quantities of cream-base medicament or any flowable composition; comprising: a revolving platform with equispaced side tabs stemming from an outer and inner base rim responsible for yielding said bi-audible and bi-tactile sensations upon interaction with ticker tabs projecting form the bottom exterior wall of the house; a threaded screw-complex that interacts with an elevator to transport the medicament upwards; a house that confines an inner chamber to store the medicament; an applicator pad with a center outlet where the composition exits the chamber; and a safety cap. Equispaced digit tabs on the outer side wall of the rotatable platform indicate the amount to be delivered. The platform rotates 18° clockwise per actuation against equispaced line demarcations on the house delivering roughly a $1/20^{th}$ of a milliliter of composition.

20 Claims, 10 Drawing Sheets

Rear View

Front View

Top View

Figure 19
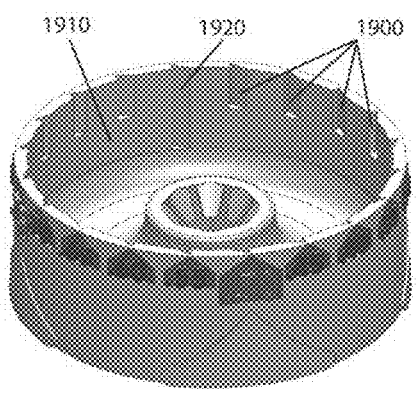
Figure 20
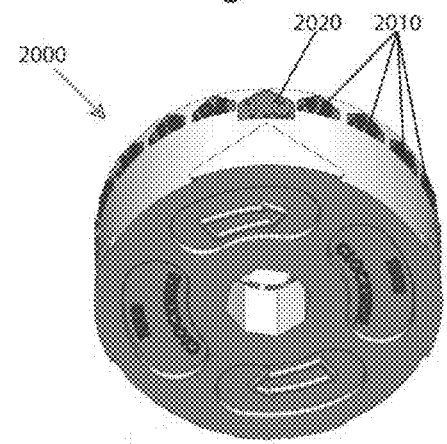
Figure 21
Figure 22
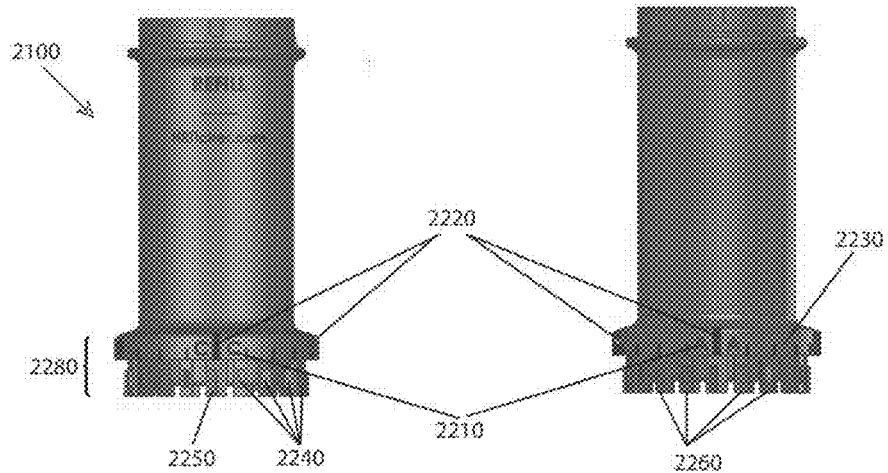
Figure 23
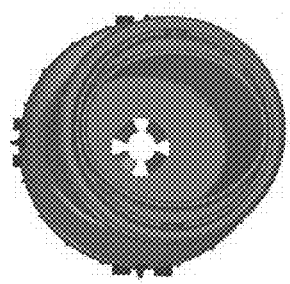
Figure 24
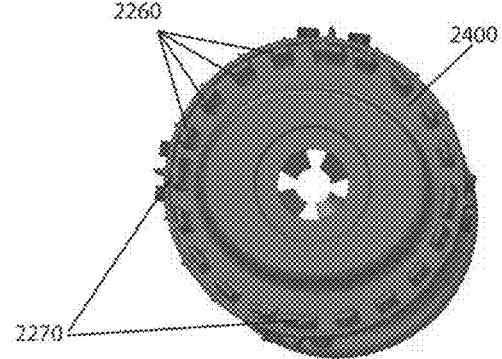

VISUAL, BI-AUDIBLE, AND BI-TACTILE METERED-DOSE TRANSDERMAL MEDICAMENT APPLICATOR

PRIORITY PATENT APPLICATION

This non-provisional patent application claims priority to U.S. provisional patent application Ser. No. 61/443,029; filed on Feb. 15, 2011 by the same applicant as the present patent application. This present patent application draws priority from the referenced provisional patent application. The entire disclosure of the referenced provisional patent application is considered part of the disclosure of the present application and is hereby incorporated by reference herein in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the disclosure herein and to the drawings that form a part of this document: Copyright 2009-2011, Ramiro M. Perez; All Rights Reserved.

TECHNICAL FIELD

A dispenser is disclosed for flowable cream-base medicaments, specifically; a unidirectional rotatable platform attached to a screw that is slipped into a barrel where it is secured in place and it joins the said components that house an elevator. Upon clockwise rotation of the rotatable platform against the barrel, the elevator rises and a fixed amount of flowable composition discharges from an output orifice in the center of the dispenser.

BACKGROUND

American compounding pharmacists are increasingly dispensing hormone replacement therapy (HRT) cream-base medicines due to raised awareness of its safety profile and benefit in relieving symptoms of hormone imbalance. The challenge to dispense accurate amounts of cream-base medicine continues since delivery device options have been very limited. Not so long ago, a prevalent option for administering cream-base HRT employed the use of ⅛, or ¼ teaspoonfuls, (looking much like an ice-cream sampling spoons) partaking in a common practice called, "eye balling". Syringes are still commonly used today in the delivery of hormone replacement therapy; whereby the pressing of the plunger pushes the cream out of the chamber through the small syringe orifice (needle excluded), and the user is able to get the correct dose by counting number differences or the number of line markings passed by the indicator.

New metered only transdermal applicators have shown some interest amongst providers and consumers. For example, pumps have been extensively employed where the user depresses a pump that delivers a "somewhat" fixed volumetric amount. (There seems to be a' lot of skepticism on the actual accuracy of these devices, especially dosing differences from the first to the second pump). Furthermore, pharmacists and physicians often have to adjust their dosing by taking into account large and inadequate volumetric amounts delivered by these metered-only devices. (i.e. 0.6, 0.7, 0.9 ml per pump). Needless to say, there is extensive variability between pumps.

U.S. Pat. No. 7,213,994 B2, as disclosed, allows for the delivery of a, "Predetermined" amount of cream through an opening in the cap. Basically, when the base is rotated 90° clockwise, an audible and tactile, "Click" is supposed to be heard translating to the delivery of a predetermined amount of cream. Furthermore, the patent claims a positive sensory feedback mechanism that confirms a desired amount of cream dispensed. The device is described as producing; in most cases, an audible sound upon a 90-degree clockwise rotation. However, consumers have reported a lack of audible sound or tactile feel on several cases, especially when the rotatable base is left in between clicking segments for prolonged periods of time; which makes it enormously difficult for consumers to apply a desired dose. The problem may be highly attributed to poor design, manufacturing defects, and poor quality assurance. To make matters worse, the said patent only delivers 0.476 g of cream-base medicament of a specific density per 180° displacement of the base past the barrel, (or per 2-clicks as reported by the company using the Medisca® HRT Cream Base). Thus, falling short from the needed 0.5 gram standard dosing requirement.

Although both types of metered only transdermal applicators have gained some popularity amongst U.S. compounding pharmacies, (especially if compared to other delivery devices, like syringes, metered screw-on caps, pea-sized spoons, etc.) the greatest challenge faced by these devices, is convincing users, and especially health providers that a "Click" or a "Pump" translates to a specific dose. Therefore, prescribers still refrain from writing in their scripts a dose based on clicks or pumps. Instead, for several decades, providers and patients seem to favor dosages based on a number scale or with some form of graduated line markings. Further, poor mechanical design, and 90 degrees, "click" limitations may be undesirable features to other consumers and providers. In this patent we have solved most the frustration medical prescribers and patients face today when it comes to selecting a useful device for delivering customary doses of transdermal hormone replacement therapies, as well as other uses unknown as of now. The present device offers consumers the delivery of calibrated volumetric amounts of cream-base medicament, a graduation area that allows consumers to visually measure a specified dose, the delivery of smaller, yet consistent volumes if desired, concurrent bi-audible, and bi-tactile features to provide dosing reassurance, and superior flexibility in the dosing of cream-base medicaments without the limitations of, "pumps" or, "clicks" posed by metered only devices.

SUMMARY

Several embodiments are disclosed, in which a novel device employs a unidirectional rotational mechanism where visual, audible, and tactile elements work together synergistically for the delivery of calibrated volumetric amounts of topical cream-base medicaments of a specified density, or any other flowable material if warranted. The interaction of primary and secondary ticker tabs stemming from the bottom exterior wall of the house, and corresponding major, minor, and redundant side ticks stemming from the rotatable platform; which, allows for the delivery of specific volumetric amounts of cream-base medicaments, has not been elucidated until now.

Moreover, the interaction and involvement of selective ticker tabs stemming from the clicking zone of the house and corresponding major, minor, and redundant side ticks stationed on the rotatable platform; which, are responsible for creating two different types of audible sounds and tactile sensations to the user depending on the angular displacement of the rotatable element against the house from a predetermined point of reference will be disclosed in detail.

The term 'housing element', or 'house' will be used to denote a barrel, side ticks as an alternative name to side tabs, and composition as an alternative name to cream-base medicament as disclosed. One example embodiment of the dispensing apparatus includes a unidirectional rotatable platform that engages the head-bolt of a left threaded screw-complex that can be slipped into the inner chamber of the housing element and secured in place by cooperation of a snap-ring and locking tabs located on the bottom wall of the house. Once inside, the screw interacts with an elevator that fits tightly against the wall of said inner chamber. Upon clockwise axial movement of the rotatable platform against the house, audible and tactile sensations can be perceived by the user at every 18 degrees of rotation; However, the type of sound depends if the 18° rotation of the platform is directed to a minor digit tab (minor tick note; soft click) or to a major digit tab (major tick note; louder sound) since different ticker tabs are involved and interact with major, minor, or redundant side ticks depending on the displacement of the rotatable platform against the house from a predetermined point of reference. The elevator rises and pushes upward the flowable contents of such chamber, exiting through an output orifice located at the center of a dispenser, which is secured to the upper end of the house providing a surface to apply the cream or gel directly onto the skin. A removable cap with a plug to retard evaporation of the cream-base medicament is stationed on top of the dispenser. As the platform rotates, the user is able to count the number of equispaced digit tabs on the rotatable platform past the markings on the first end of the house for determining a desired dose. A left threaded rod interacts with an elevator equipped with a top and bottom edge seal useful in preventing a cream smudge trail or any visible cream from being left behind and causes it to rise. A bi-audible mechanism is in place for determining set volumetric amounts dispensed upon an 18° clockwise rotation of the rotatable platform against the house. A 90°, 180°, 270°, or a 360 degree displacement of the rotatable platform against the house from a predetermined point of reference produces a peculiar audible and tactile sensation on the user, referred here as the first sound. Likewise, displacement other than a 90°, 180°, 270°, or 360 degrees from a predetermined point of reference, produces a different yet distinct audible and tactile sensation on the user, referred here as the second sound. An 18° rotation of the base platform translates to a 0.05 numerical difference on the exterior wall of the rotatable platform, or one digit tab movement of the rotator past the house. It follows that a 90° rotation translates to a 0.25 numerical difference on the exterior wall of the rotatable platform with respect to the house. The device has been configured to deliver roughly one gram of a specified cream of a specific density (or 1.03 g of water at 25° C.) for every 360° rotation of the rotatable platform against the house. A dispenser pad is available to aid in the application of the cream-base medicament if so desired by the consumer.

BRIEF DESCRIPTION OF THE DRAWINGS

Features of the various embodiments will be fully appreciated through the following detailed discussion. Reference is made to the figures consisting of:

FIGS. 15-28 illustrate alternative embodiments of an apparatus for dispensing any flowable composition in reference to the various embodiments.

DETAILED DESCRIPTION

Figure 1A:
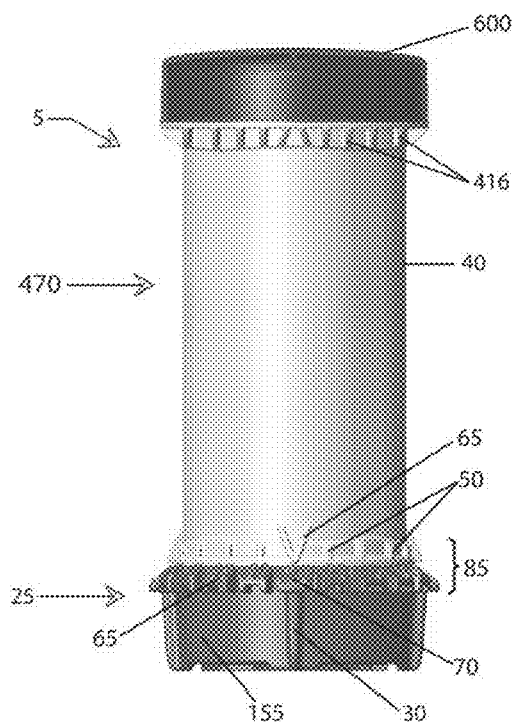
FIG. 1A which is a front perspective view of a complete assembled apparatus for dispensing any flowable composition in reference to the various embodiments.

In various embodiments, a transdermal, visual, bi-audible and bi-tactile to the senses cream applicator with calibrated, equispaced line demarcations, and supplemental numerical legend, each positioned at a predetermined 18 degree angle from one another translating to the delivery of roughly a $\frac{1}{20}^{th}$ milliliter of flowable cream-base medicament of a specific density is described in detail herein.

FIGS. 1-14 depict an embodiment of a dispensing apparatus 5 with regard to this novel system for the delivery of cream, gel, ointment, or any suitable flowable substance of interest.

This novel applicator 5 comprises the following six vital elements: a rotatable platform 25, a house 470, a screw-complex 200 (see FIG. 8), an elevator 325, a dispenser 500, and a safety cap 600.

All parts can be made of rigid plastic or a similar material, but the preferred material is polypropylene. Prototypes can be designed in ProJet, Stereolithogray (SLA), or Acura 25.

Figure 1B:
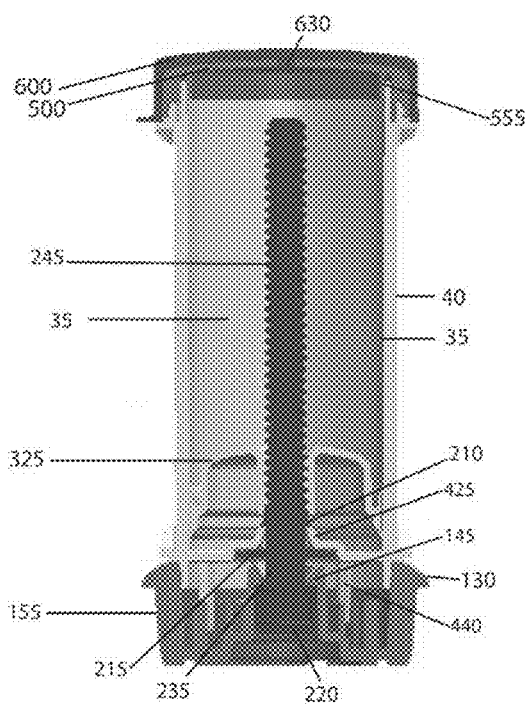
FIG. 1B which is a vertical cross sectional view of an assembled dispenser.

FIGS. 1A and 1B introduces the assembled apparatus 5 as a complete unit (FIG. 1A) or as a vertical cross sectional view, (FIG. 1B) where the house 470 is located in between the dispenser 500 and the rotatable platform 25. The elevator 325 rests at the bottom of the inner chamber of the house 470 where the left threaded screw-complex 200; which is secured in between the house 470 and the rotatable platform 25 causes it to rise upon clockwise rotation of the rotatable platform 25. A safety cap 600 with a plug 630 to retard evaporation and prevent contamination of the cream is situated on top of the dispenser 500; where the safety cap 600, which can snap into the dispenser end of the house by cooperation of the semi-annular rib 645 on the inner wall of the safety cap 600 and the safety rim 408 on the outer wall of the dispenser end 401 of the house 470 adjacent to the upper rim 415. The dispenser 500 gets locked into the dispenser end 401 of the house 470 by interaction of the annular groove 540 on its inner side wall 550 and the peripheral rim 407 on the outer wall of the dispensing end 401 of the house 470. An outer slim wall 555 fits in between the elevator's outer side wall 315 and the inner side wall 35 of the house 470. The elevator 325 and screw shaft 245 inside the house 470 interact only to allow upward movement upon clockwise rotation of the rotatable platform 25. The house locking tabs 425 override the snap ring 210 landing into the orbit area 240 and locking the screw-complex 200 in place only to allow axial movement. Platform locking tabs 145 override the bolt-head 220 and secure the bolt-neck 235, thereby locking the rotatable platform 25 in place. The strategic position of the bolt neck 235; which, resides in between the joined washer 215 and the bolt head 220 serves to secure the platform locking tabs 145 that stem from the bottom inner wall 105 of the rotatable platform 25 and consequently the rotatable platform 25 as a whole to prevent movement to such segment in any direction. Once the rotatable platform 25 is attached to the screw-complex 200, the only possible movement, which involves the cooperation of the rotatable platform 25 and the screw-complex 200 behaving as a single unit, is to rotate clockwise around its own axis.

With the screw-complex 200 set in place interacting with the rotatable platform 25, house 470, and elevator 325, its mechanism can be fully appreciated. The primary ticker tabs 435 interact with minor side ticks 110 on the rotatable platform 25, and produce a unique and identifiable sound depending on the displacement of the rotatable platform 25 against the house 470. Upon an 18° displacement, primary ticker tabs 435 can clear the minor side ticks 110 to land into tab rest segments 111 and produce the second sound, or they can clear the major side ticks 112 to land into different tab rest segments 111 to produce the first sound. When the secondary ticker tabs 440 clear the redundant side ticks 115 upon an 18 degree rotation of the rotatable platform 25, the first sound is also emitted by the apparatus and captured by the senses of the consumer. Therefore, primary ticker tabs interact with major side ticks concurrently when secondary ticker tabs interact with redundant side ticks. Advantageously, there are only four major side ticks 112 strategically positioned to interact with the primary ticker tabs 440 and produce a louder identifiable sound only at key displacement locations; specifically at every 90°, 180°, 270°, and 360° displacement locations from a predetermined reference point; which also corresponds to the alignment of the 0.25, 0.50, 0.75, and 1.0 major digit tabs 70 of the rotatable platform 25 with the fixed major line markings 65 of the house 470.

In addition, at these four displacement locations, (90°, 180°, 270°, and 360°) there is sound summation taking place due to the concurrent interaction of primary ticker tabs 435 with major side ticks 112, as well as secondary ticker tabs 440 interacting redundant side ticks 115; ultimately yielding a more pronounced sound and tactile sensation at these predetermined sites.

Figure 1C:
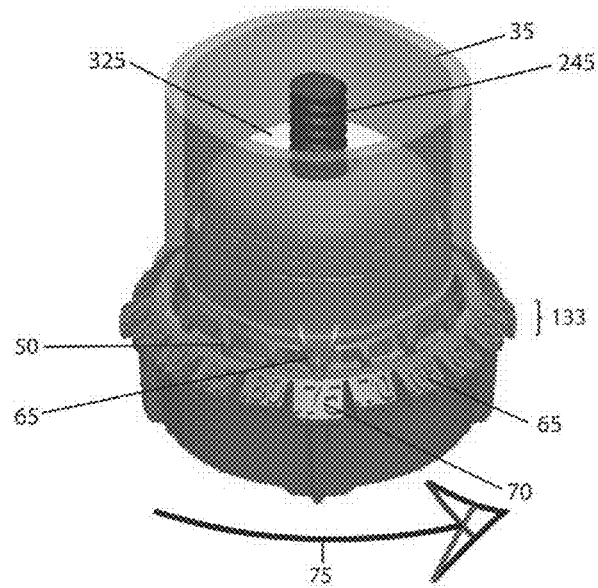
FIG. 1C which is a magnified horizontal cross-sectional view of the bottom end of the assembled dispensing apparatus with an arrow positioned just below to indicate rotational orientation of the rotatable platform.

FIG. 1C presents a horizontal cross-section of the lower end of an assembled apparatus emphasizing major 70 and minor 65 digit tabs. There are twenty digit tabs arranged in reverse ascending order along the equispaced digit zone 133, and each digit tab is separated by an 18° angle from one another. The attachment of the rotatable platform 25 with the housing 470 creates the graduation area 85; which is essential in allowing users to determine a specified volumetric dose. A cartoon arrow below the illustration 75, points to the direction of allowed movement of the unidirectional rotatable platform 25.

There are four grip tabs 30 to ease rotation. Further, the lower end of the house 470 provides equispaced extruded line demarcations to create a predetermined point of reference during rotation of the rotatable platform 25. Fixed major markings 65 and fixed minor markings 50 span along the outer circumference of the lower end of the house 470. An elevator 325 residing inside the chamber of the house 470 is attached to the screw shaft 245 and causes it to rise upon clockwise rotation of the rotatable platform 25.

Figure 2:
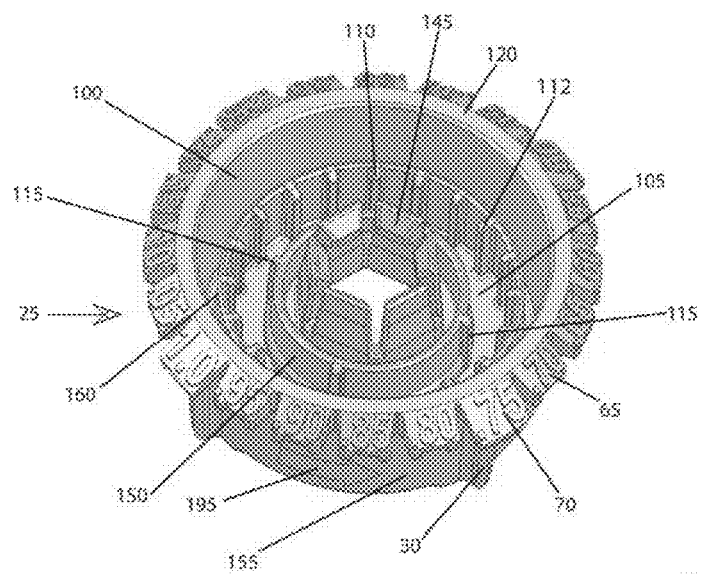
FIGS. 2, 3, and 4; which are schematic views of the rotatable platform.
Figure 3:
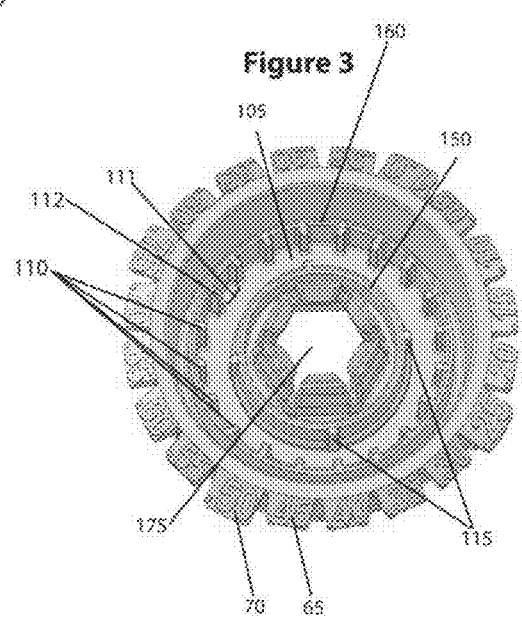
Figure 4:
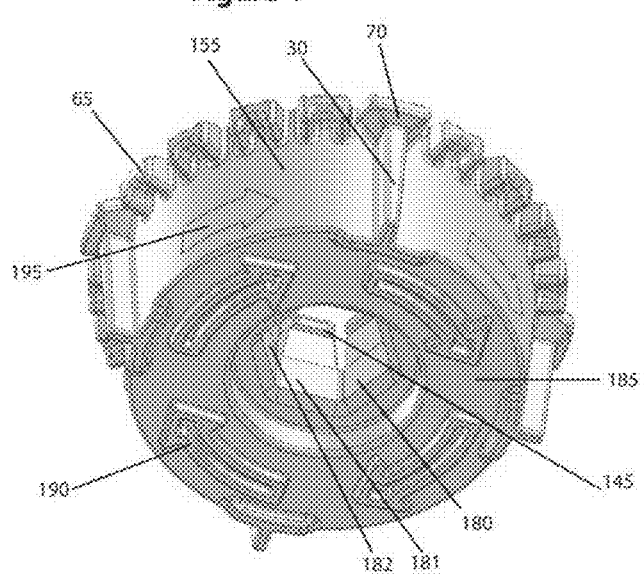
Figure 5A:
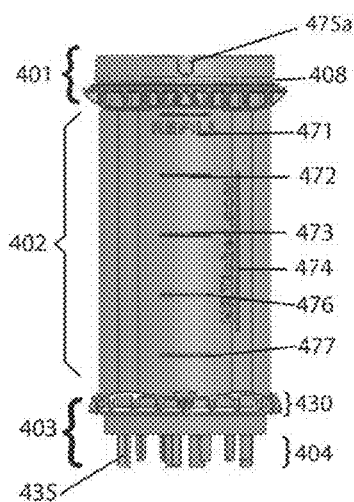
FIGS. 5A, 5B, 6, 7; which exhibit different schematic views of the house.
Figure 5B:
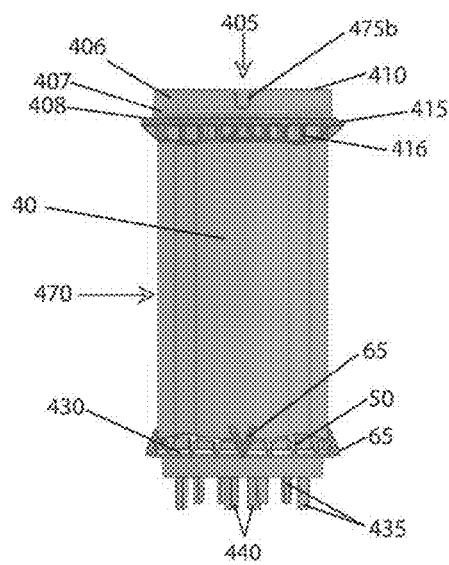
Figure 6:
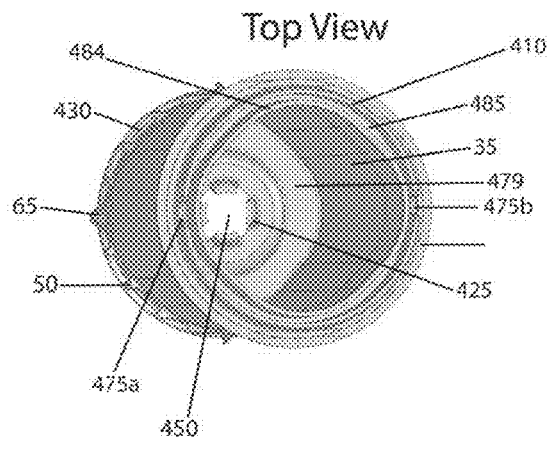
Figure 7:
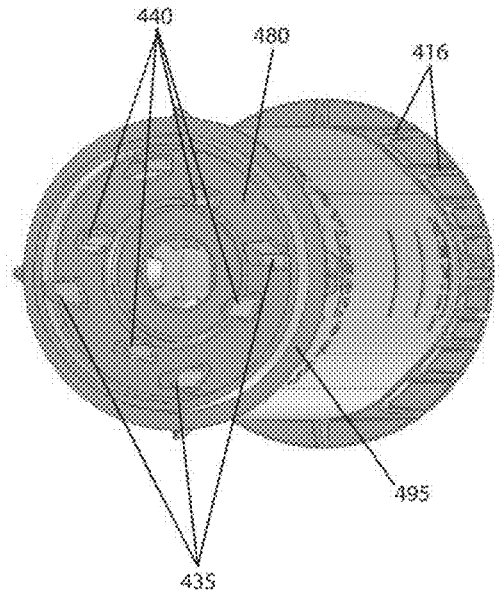

FIGS. 2-4 are schematic views of the rotatable platform 25, where the outer side wall 155 of the rotatable platform houses the equispaced digit zone 133 which comprises four raised major digit tabs 70, and sixteen raised minor digit tabs 65 all arranged in ascending order (by 0.05 intervals) as the platform 25 rotates clockwise against the house 470. In addition, the platform outer side wall 155 has four side grips 30; each situated right below each major digit tab 70 (positioned at 90° degrees from each other along the outer circumference) which span along the equispaced digit zone 133 to facilitate rotation of the platform 25. The platform lip 120 makes contact with the graduated ring base 495 of the house 470 to create the graduation area 85, (FIG. 1A). FIG. 4 presents the bottom end of the rotatable platform 25 where side arrows 195 and bottom arrows 190 indicate the direction of movement allowed by the rotatable platform 25.

FIG. 2 and FIG. 4 are schematic views of the rotatable platform 25 where locking tabs 145 extend upward from the center of the bottom inner wall 105, having six slanted but downward pointing locking tabs 145 which serve to override the bolt head 220 and land onto the bolt neck 235 practically fusing the screw-complex and rotatable platform 25 as one piece. The rotatable platform 25 outer base rim 160 houses sixteen minor side ticks 110 and four major side ticks 112; which interact with ticker tabs stemming from the bottom exterior wall 480 of the house 470. Additionally, four redundant side ticks 115 equispaced from one another stem from the inner base rim 150 of the platform 25 to engage with four secondary ticker tabs 440 also stemming from the outer bottom exterior wall 480 of the house 470. The inner side wall 100 of the rotatable platform 25 could potentially house major and minor side ticks as well in lieu of the outer base rim 160.

FIG. 4 presents another schematic view the rotatable platform 25 where the bottom exterior wall 185 of the rotatable platform 25 is clearly exhibited. The locking tabs 145 point inward towards the bottom of the hexagon void 175. There is one locking tab 145 stemming from each upper corner of the hexagon side wall 180, 181, 182, where the two walls join. Further, bottom indication arrows 190, and side indication arrows 195 show the direction of allowed movement of the rotatable platform 25.

The house 470, which is basically a barrel, is introduced in FIGS. 5A, FIG. 5B, FIG. 6 and FIG. 7, having three major sections. A dispenser end 401, a body 402, and a platform end 403 comprising a graduation ring 430 and a clicking zone 404. The body 402 of the house 470 consists primarily of an inner side wall 35, and the outer side wall 40; which, can accommodate a label with consumer instructions. At the dispenser end 401, there is a dispenser opening 405 used to load the cream-base medicament into the chamber of the house 470. There are two dispenser notches 475a, 475b at opposite ends of the circular upper edge 410; which guide the insertion guides 530 of the dispenser 500 to properly slip in upon pressing against the house 470. A peripheral rim 407 on the house outer side wall 40 engages with its complementary annular groove 540 on the inner side wall 550 of the dispenser 500 locking it upon pressing against the house 470.

An extruded upper rim 415 with reinforcement ribs 416 just beneath it is situated just below the circular upper edge 410 which assists in locking the dispenser 500 upon pressing against it. The inner side wall 35 of the house 470 is directly in contact with the composition and it is perpendicular to the bottom inner wall 479; which, on its center has a void with four upward projecting locking tabs 425 for accepting and locking the screw-complex 200 in place with the house 470 only to allow rotation along its own axis. The chamber upper edge 484 concludes the upper end of the chamber; which has a semi-square shape in order to maximize volume, but it is connected to the circular upper wall 406 by a wall to wall connector 485, that terminates at the top with the circular upper edge 410.

The platform end 403 of the house 470 has a raised graduation ring 430, with twenty demarcation line markings, referred here as fixed major and minor line markings (65; 50); respectively. There are four fixed major line markings 65, separated at 90° from each other along the outer circumference of the of platform end 403 of the house 470 and sixteen fixed minor line markings 50, all forming the graduation ring 430. The primary ticker tabs 435 stemming from the platform end 403 of the house interact with minor side ticks 110 stemming from the outer base rim 160 of the rotatable platform 25 producing a unique but soft second sound at every 18° of rotation depending on the angular displacement from a predetermined point of reference. In addition, the primary ticker tabs 435 also interact with major side ticks 112 stemming from the outer base rim 160 of the rotatable platform 25 to produce a louder first sound upon clearance of the primary ticker tabs 435. The secondary ticker tabs 440 interact with the redundant side ticks 115 of the rotatable platform 25 to produce the louder first sound upon completion of an 18° movement by the platform to any major digit tab 70 position, (or a 90° predetermined angular displacement from a fixed point of reference) as well as a specific vibration that corresponds to the tactile component that users can sense. Furthermore, an even louder sound and greater tactile sensation is achieved by summation of ticker tabs to side tick interactions; specifically, primary and secondary ticker tabs interacting with major and redundant side ticks, simultaneously, where the landing of all ticker tabs take place upon completion of an 18° displacement into the major digit tabs 70. A screw orifice 450, accepts the screw-complex 200 and the locking tabs 425 override the snap ring 210 landing into the orbit area 240 of the screw-complex 200 where the screw-complex 200 is practically locked to the house 470.

Figure 8:
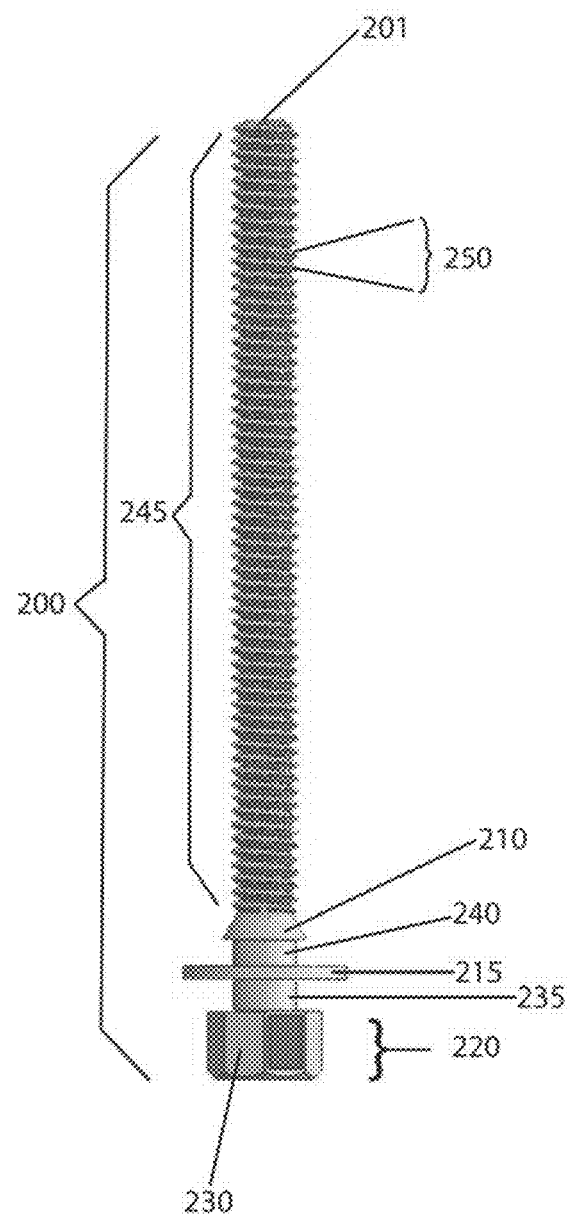
FIG. 8 which is a side view of the screw-complex comprising a head bolt, joined washer, snap ring, and screw.

FIG. 8 illustrates the bolt head 220, joined washer 215, snap ring 210, and a screw 245. Once combined, all these components form the screw-complex 200. The pitch 250 is the distance between threads; which, causes a predetermined but specific elevation on the elevator; ultimately having a role on dosing. The screw end 201 of the screw-complex 200 continues downward along the screw 245 until the threading stops at a snap ring 210; which, upon passing, it secures the screw-complex 200 to the house 470 cooperating with four upward slanted locking tabs 425 stemming from the bottom inner wall 479 of the house 470 and a joined washer 215 that serves as a securing mechanism. The bolt head 220 has six equal head side walls 230. The bolt neck 235 is the area between the bolt head 220 and joined washer 215; which serves to secure the rotatable platform 25.

Figure 9:
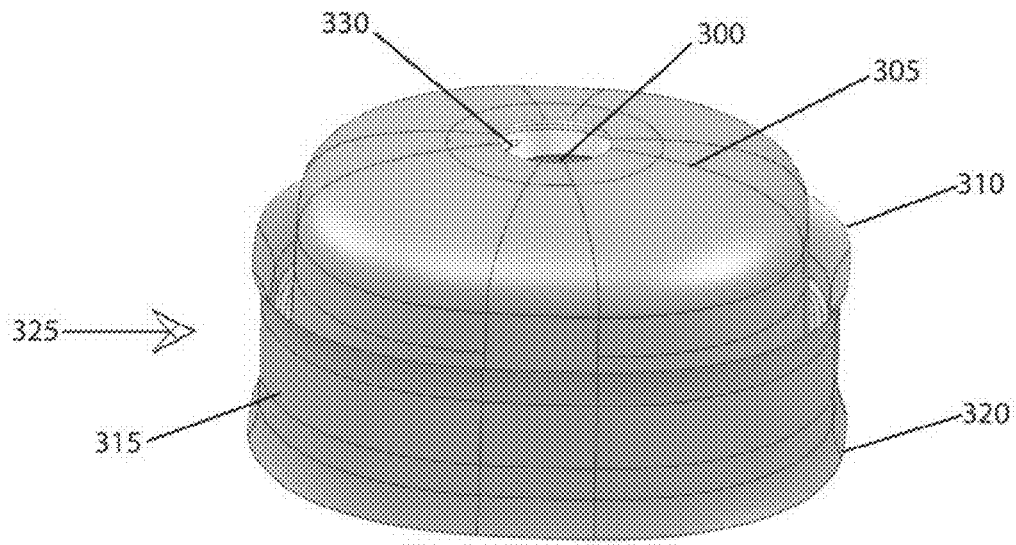
FIG. 9 and FIG. 10 which present 3-dimensional views of the elevator displaying a top and a bottom edge seal, a top outer wall, and a female threaded ring, and a center void.
Figure 10:
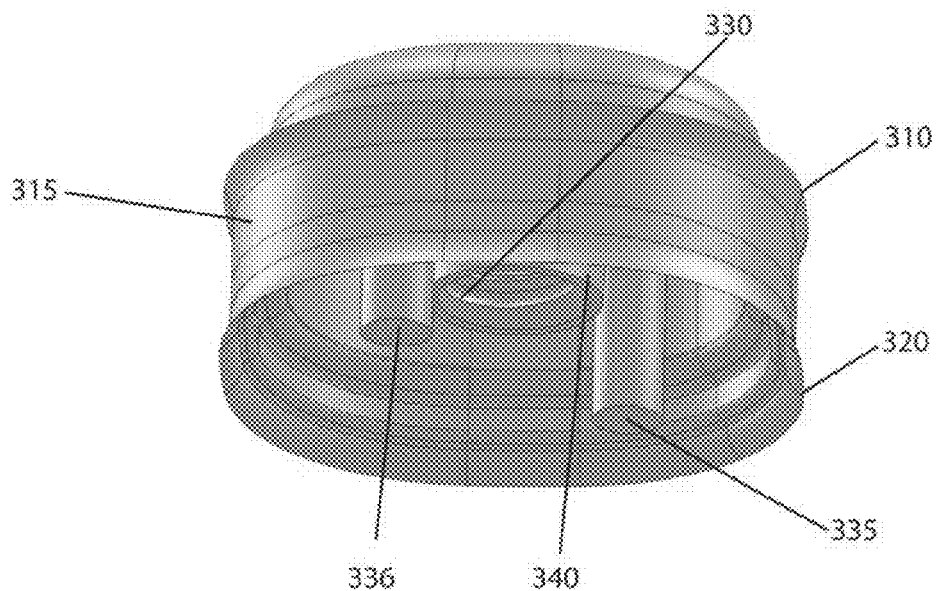

FIG. 9 is a schematic view of the elevator 325. The elevator pushes the cream-base medicament, which resides in a closed chamber upwards, to exit through an outlet 505 upon movement of the rotatable platform 25. The top outer wall 305 is dome shaped with a concave outer side wall 315 where the top edge seal 310 and bottom edge seal 320 are at opposite ends; which, also serves to prevent cream form smudging or being left behind. On the center of the elevator 325, there is a ring void 300 that interacts with the treaded area of the screw 245. The bottom view of the elevator 325 is presented on FIG. 10 where the female threaded ring 330 appears around the center of the elevator 325, as well as the intrinsic wall 340 where it stems from. There are two assembly stoppers 335, 336 to prevent damage to the elevator by the assembly tooling.

Figure 11:
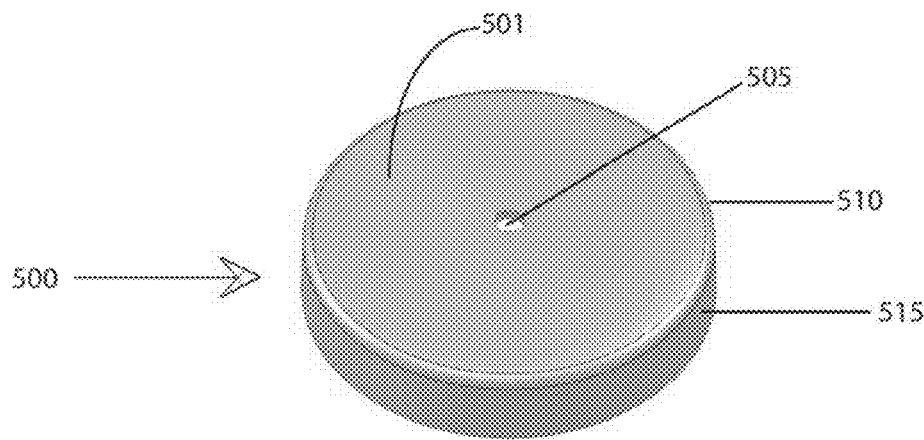
FIG. 11 and FIG. 12; which depict two perspective views of an isolated dispenser; with the top and bottom views exposed.
Figure 12:
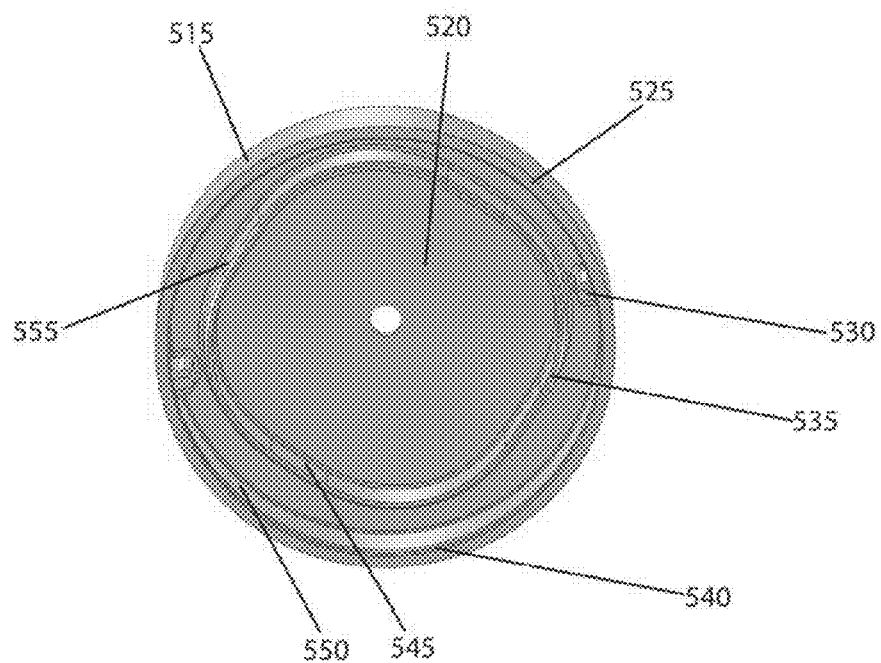

FIG. 11 is a schematic view of the dispenser 500 where the dispensing pad 501 serves as a dispensing element. The outlet 505 allows the cream-base medicament to be expelled and perhaps temporarily reside there until application. The smooth upper edge 510 connects the outer side wall 515 and dispensing pad 501 together. FIG. 12 is a schematic view of the dispenser 500, where the bottom side of the dispenser is exposed, causing the following to appear; the top inner wall 520, the inner side wall 550, and a dispenser bottom edge 525. An additional wall exists to seal the cream inside the chamber and prevent dispersion. It consists of an inner slim wall 545, an outer slim wall 555, and the slim edge 535. There are two insertion guides 530 on the inner side wall 550 at opposite positions along the circumference to fit into the dispenser notch 475*a*, 475*h* allowing the dispenser to slip onto the dispenser end 401 of the house 470. The dispenser 500 snaps tightly into the house 470 and cannot be detached by cooperation of the annular groove 540 and the peripheral rim 407 of the house 470.

Figure 13:
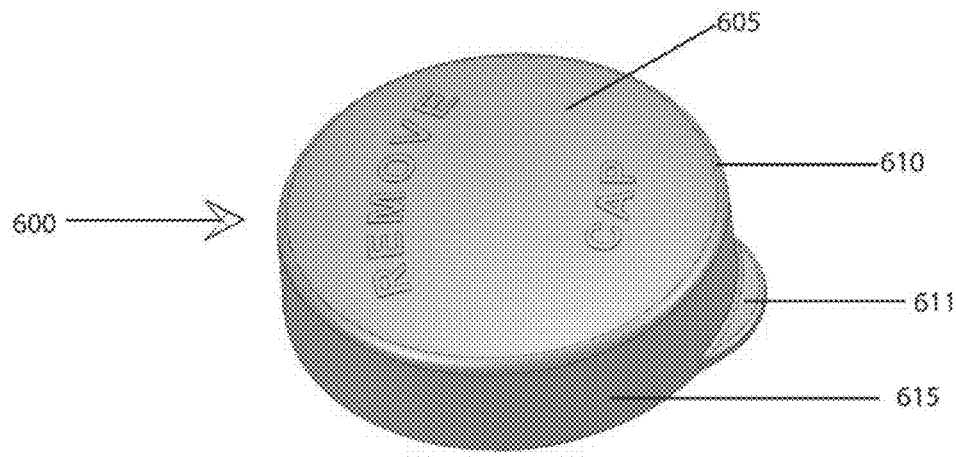
FIG. 13 and FIG. 14; which present two perspective views of the safety cap suspended in mid air.
Figure 14:
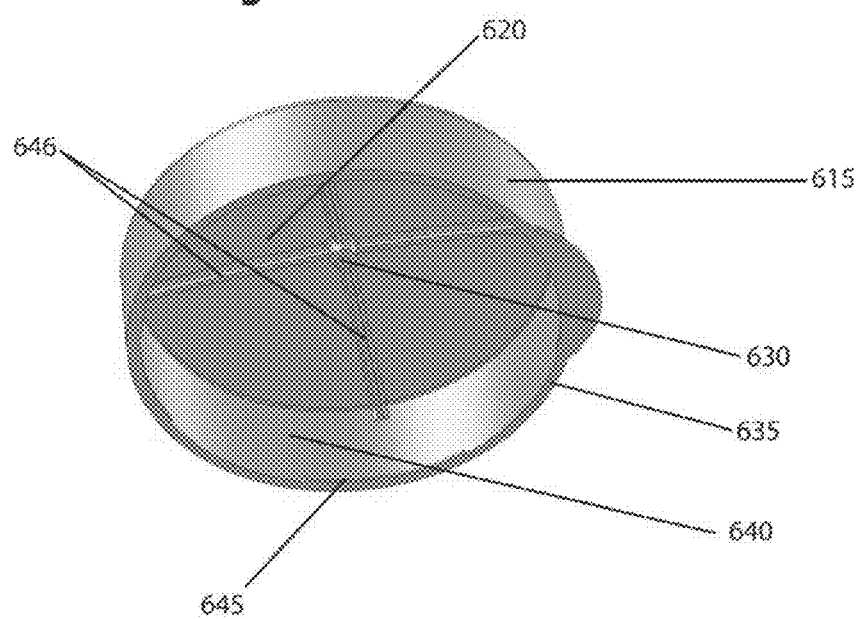
Figure 15:
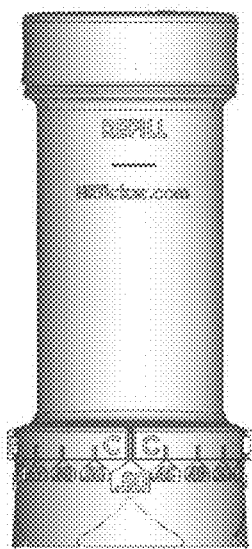
Figure 16:
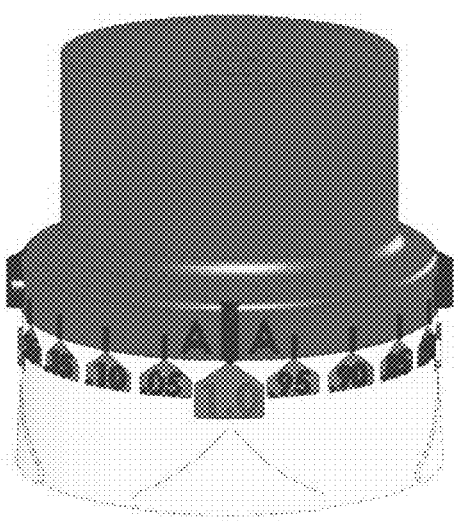
Figure 17:
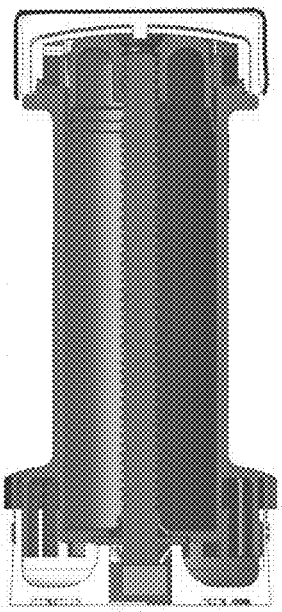
Figure 18:
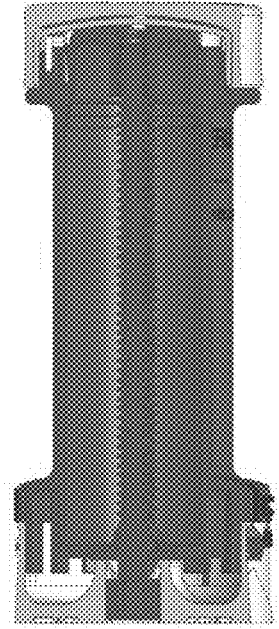

FIGS. 13 and 14 are schematic views of the safety cap 600 exhibiting the top outer wall 605, and smooth upper edge 610, an outer side surface 615, a lower edge 635, an inner side wall 640, an inner top wall 620, a semi-annular rib 645, reinforcement ribs 646, and a plug 630.

Pre-Assembly: This involves the collaboration four components; the screw-complex 200, house 470, elevator 325 and rotatable platform 25. The screw end 201 and the screw-complex 200 get inserted to the house 470 past the house locking tabs 425. Once the locking tabs 425 override the snap ring 210, the screw-complex 200 gets trapped in the house 470 in parallel with the chamber's inner side wall and it's only able to rotate axially. Tooling facilitates assembly of the elevator 325 where counterclockwise rotation of the screw-complex 200 allows the elevator 325 to get screwed into the bottom end of the house 470. The hexagonal shape of the bolt head 220 allows it to be attached to an electrical female hexagonal-socket and yield assembly of the elevator 325 into the bottom end of the house 470 efficiently. Next, the rotatable platform 25 is slipped into the bottom end of the house 470 where the locking tabs 145 overrides the bolt head 220 to land into the bolt neck 235 where the platform locking tabs 145 secure the rotatable platform 25 into the other said components (25, 470, 200, 325) in a tight fit, practically fusing the rotatable platform 25 to the house-screw-complex-elevator components. The preassembled unit, along with the dispenser 500, and security cap 600, (assembly add-ons) can be shipped as a single unit or in large quantities.

Assembly: Compounding pharmacists or other dispensing personnel can place a desired quantity of the flowable cream-base medicament inside the chamber of the housing 470 through the dispenser opening 405. The dispenser 500 gets positioned to fit into the housing 470 through insertion guides 530 that fit into the dispenser notch 475*a*, 475*b*. Upon pressing, the annular groove 540 fastens into the peripheral rim 407 of the house 470. Once locked, the dispenser cannot be removed by the average consumer unless a skilled provider or technician, using a pointy tool can carefully pull the dispenser's bottom edge 525 and displace the dispenser 500 outwards. Once in place, the applicator gets primed (air removed) to a desired setting by rotating the rotatable platform clockwise; as allowed. We recommend technicians and dispensers to partially prime the unit to prevent spilling; especially if transporting to different altitudes as pressure changes may force the cream-base medicament out of the device. The security cap 600 can be inserted to prevent medicament contamination, spill, and retard medicament evaporation by sealing the outlet 505. The security cap 600 can also be fastened to a tight fit if one applies additional force by cooperation of the semi-annular rib 645 and safety rim 408. A thumb tab 611 is placed near the lower edge 635 and lower outer side wall 615 of the safety cap 600 to ease removal.

Audible and Tactile Mechanism

Minor Tick Note: This is the sound and tactile sensation caused by the interaction of primary ticker tabs 435 stemming from the bottom exterior wall 480 of the house 470 with minor side ticks 110 stemming from the outer base rim 160 of the rotatable platform 25 due to an 18° displacement of the rotatable platform 25 against the house 470 to any predetermined minor digit tab (other than digit tabs 0.25, 0.50, 0.75, and 1.0). A soft and distinct sound and tactile sensation is captured by the user upon clockwise rotation of the rotatable platform 25 against the house 470 of the apparatus at any of these predetermined angular displacements allowed.

Major tick Note: This is the sound and tactile sensation caused by interaction of primary ticker tabs 435 and major side ticks 112 plus the concurrent interaction of secondary ticker tabs 440 stemming from the bottom exterior wall 480 of the house 470 with redundant side ticks 115 stemming from the inner base rim 150 of the rotatable platform 25 due to an 18° displacement of the rotatable platform 25 with respect the house 470 to the following predetermined major digit tabs, 0.25, 0.50, 0.75, and 1.0. This summation, and thus amplification of sound and tactile sensations makes for a bi-audible and bi-tactile apparatus.

Refill Reminder Indicator: As presented on FIG. 5A, a small raised horizontal bar 472 near the upper rim 415 serves to indicate to the consumer their cream-base medicament may be running low. Further, the word, "refill" positioned right beneath the upper rim is shown embossed 471 to also remind consumers their medicament may be running-out. A second raised horizontal line 473 sits just about the middle part of the house 470 to indicate pharmacy technicians or other dispensing personnel a rough estimation of a half-filled applicator in cases where the prescribed amount is half the usual amount prescribed, given that one full container may be the norm. There are two additional horizontal lines 476, 477 to also help in indicating levels of a 75% or a 100% composition-filled applicator; respectively. A vertical bar 474, also shown in FIG. 5A, serves as a guide to properly position an indication label on the face of the outer side wall 40 of the house 470.

Variations

Figure 25:
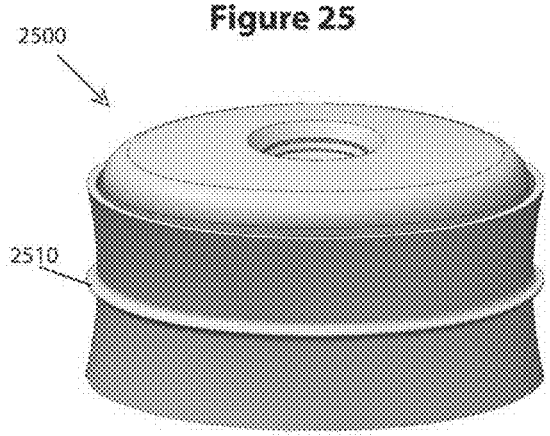
Figure 26:
Figure 27:
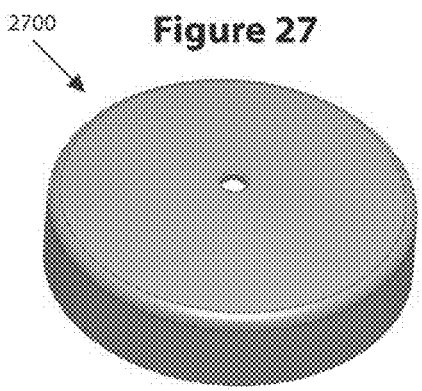
Figure 28:
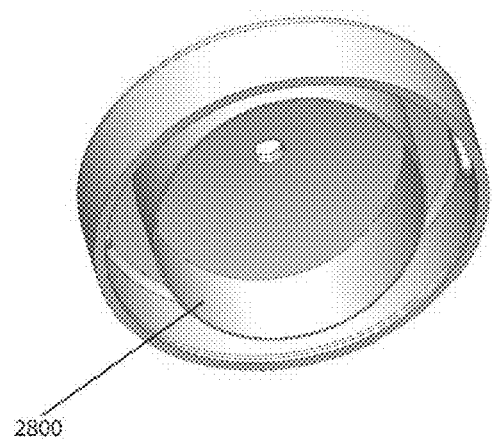

A variation of the current design is seen in on FIGS. 15-28 where the cream-base medicament is stored in an enclosed cylindrical shaped chamber. In Addition, the major yielding tabs 2270, and minor yielding tabs 2260 emit a sound at every 18° rotation of the rotatable platform 2000 past the house member 2100. The main difference is that this device produces an almost identical sound and tactile sensation at every 18° rotation of the rotatable platform 2000 past the house member 2100. In addition, extruded grapheme letters 2210, (A,A, B,B, C,C, and D,D) and major line markings 2220 are located in the graduation ring 2230 of the platform end 2280 of the house 2100. The rotatable platform 2000 has four major slanted grooves 1920 and sixteen minor slanted grooves 1900 on the inner wall 1910 of the rotatable platform 2000 that engage with four major teeth-like projections 2250 and sixteen minor teeth-like projections 2240 stemming from four major yielding tabs 2270 and sixteen minor yielding tabs 2260 that originate from the bottom exterior wall 2400 of the house 2100; as seen on FIGS. 19-24. The Dispenser 2700 seen on FIGS. 27-28 has a slightly different inner slim wall 2800 to fit into said elliptical chamber where the composition is stored. The elevator 2500 with an enhanced mid-rim seal 2510 is seen on FIGS. 25-26 with its cylindrical shape configured to fit on the said house chamber. Each 18° rotation of the rotatable platform 2000 against the house 2100 is configured to deliver a $\frac{1}{20}^{th}$ milliliter of flowable composition. A bi-tactile and bi-audible mechanism is also produced with this design. A first sound corresponding to digit tabs 0.25, 0.50, 0.75, and 1.0 is configured by increasing the depth of fall of major teeth-like projections 2250 into major slanted grooves 1920. A second sound at positions other than 0.25, 0.50, 0.75, and 1.0 is produced where the major teeth-like projections 2250 and minor teeth like projections 2240 land into minor slanted grooves 1900 where depth of fall of teeth-like projections into slanted grooves is rather shallow.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus comprising:
    a house including a plurality of equispaced primary ticker tabs and a plurality of equispaced secondary ticker tabs at a first end of the house;
    a rotatable platform rotatably coupled to the first end of the house, the rotatable platform including a plurality of equispaced major digit tabs and a plurality of equispaced minor digit tabs arranged along an outer side wall of the rotatable platform to complement key reference markings on the first end of the house, the rotatable platform including a plurality of major side ticks and a plurality of minor side ticks arranged on an outer base rim of the rotatable platform, each of the plurality of major side ticks being larger than each of the plurality of minor side ticks, the rotatable platform including a plurality of redundant side ticks arranged on an inner base rim of the rotatable platform, the outer base rim being concentric with the inner base rim, the outer base rim being of a larger diameter than the inner base rim, the plurality of major side ticks and the plurality of redundant side ticks configured to interact simultaneously with the primary ticker tabs and the secondary ticker tabs, respectively, to produce a first sound with rotation of the rotatable platform, the plurality of minor side ticks configured to interact with the primary ticker tabs to produce as second sound with rotation of the rotatable platform, the first sound being an audibly distinct and different sound relative to the second sound;
    a screw-complex coupled to the rotatable platform and positioned within an interior region of the house;
    an elevator coupled to the screw-complex and configured to rise within the interior region of the house with rotation of the rotatable platform; and
    a dispenser coupled to a second end of the house.

2. The apparatus as claimed in claim 1, further including a safety cap configured to cover the dispenser and to retard evaporation and prevent contamination or spillage.

3. The apparatus as claimed in claim 1, wherein there are tour major digit tabs and sixteen minor digit tabs.

4. The apparatus as claimed in claim 1, wherein there are four major side ticks, sixteen minor side ticks, and four redundant side ticks.

5. The apparatus as claimed in claim 1, being configured to deliver approximately $1/20^{th}$ of a milliliter of a cream-base medicament for each first or second sound produced by each minor interval rotation (18°) of the rotatable platform.

6. The apparatus as claimed in claim 1, being configured to deliver approximately $1/4^{th}$ of a milliliter of a cream-base medicament or each first sound produced with each major interval rotation (90°) of the rotatable platform.

7. The apparatus as claimed in claim 1, wherein the second sound is produced with each 18° rotation of the rotatable platform, except when the first sound is produced.

8. The apparatus as claimed in claim 1, wherein a first tactile sensation is produced with each first sound produced with the rotation of the rotatable platform.

9. The apparatus as claimed in claim 1, wherein a second tactile sensation is produced with each second sound produced with the rotation of the rotatable platform.

10. The apparatus as claimed in claim 1, configured to deliver roughly a $1/20^{th}$ of a milliliter of cream-base medicament per actuation (18°), while rendering bi-audible and bi-tactile sensations to a consumer during use.

11. The apparatus as claimed in claim 1, wherein the rotatable platform further comprising: twenty equispaced digit tabs along the outer side wall of the rotatable platform to complement key reference markings on the platform end of the house allowing for the delivery of specific volumetric doses of the flowable cream-base medicament upon rotation.

12. The apparatus as claimed in claim 1, wherein the rotatable platform further comprising: sixteen extruded equidistant minor digit tabs span along an outer upper side wall of the rotator platform, the digit tabs being arranged as four consecutive equispaced minor digit tabs followed by a major digit tab in increasing number as the rotatable platform rotates clockwise.

13. The apparatus as claimed in claim 1, wherein the rotatable platform further comprising: four extruded equidistant major digit tabs span around an upper outer side wall of the rotatable platform.

14. The apparatus as claimed in claim 1, wherein the plurality of minor side ticks are arranged at 18° apart from one another, except where the major side ticks exist.

15. The apparatus as claimed in claim 1, wherein the plurality of major side ticks are arranged at 90° apart from one another and slightly taller than the plurality of minor side ticks.

16. The apparatus as claimed in claim 1, wherein the plurality of redundant side ticks are arranged at 90° apart from one another.

17. The apparatus as claimed in claim 1, wherein the house member further comprising: sixteen extruded equidistant fixed minor line markings around an outer wall of the first can of the house.

18. The apparatus as claimed in claim 1, wherein the house member further comprising: four extruded equidistant fixed major markings around an outer wall of the first end of the house.

19. The apparatus as claimed in claim 1, wherein the rotatable platform further comprising: four raised thumb grips stemming from an outer side wall of the rotatable platform, allowing for a better grip as the platform rotates, and for pinpointing the major digit tabs.

20. The apparatus as claimed in claim 1, wherein the house further comprising: a clicking zone with primary ticker tabs configured to interact with the plurality of major side ticks and the plurality of minor side ticks, and secondary ticker tabs configured to interact with the plurality of redundant side ticks, wherein a first tactile sensation is produced in the clicking zone with each first sound produced with the rotation of the rotatable platform, and wherein a second tactile sensation is produced in the clicking zone with each second sound produced with the rotation of the rotatable platform.

* * * * *